(12) United States Patent
Jang et al.

(10) Patent No.: US 9,095,532 B2
(45) Date of Patent: *Aug. 4, 2015

(54) **COMPOSITION FOR ANTI-AGING OR ANTIOXIDANT COMPOSITION CONTAINING PLANT STEM CELL LINE DERIVED FROM CAMBIUM OR *PANAX GINSENG* INCLUDING WILD GINSENG AND GINSENG AS ACTIVE COMPONENTS**

(71) Applicant: Unhwa Corporation, Jeonju-Jeonbuk (KR)

(72) Inventors: Mi Ok Jang, Jeonju Jeollabuk-Do (KR); Min Jung Lim, Jeonju Jeollabuk-Do (KR); Il Seok Oh, Iksan Jeollabuk-Do (KR); Dae Hee Lee, Jeonju (KR); Eun Kyong Lee, Iksan (KR); Young Woo Jin, Jeonju (KR)

(73) Assignees: Unhwa Corporation (KR); Young Woo Jin (KR); Eun Kyong Lee (KR)

( * ) Notice: Subject to any disclaimer, the term of this patent is extended or adjusted under 35 U.S.C. 154(b) by 0 days.

This patent is subject to a terminal disclaimer.

(21) Appl. No.: 13/863,817

(22) Filed: Apr. 16, 2013

(65) Prior Publication Data

US 2013/0302287 A1    Nov. 14, 2013

Related U.S. Application Data

(63) Continuation of application No. 12/997,858, filed as application No. PCT/KR2009/003176 on Jun. 12, 2009, now abandoned.

(30) Foreign Application Priority Data

Jun. 13, 2008   (KR) .................... 10 2008 0056008

(51) Int. Cl.
   *A61K 36/25*     (2006.01)
   *A61K 8/97*      (2006.01)
   *A61Q 19/08*     (2006.01)
   *A61Q 19/00*     (2006.01)

(52) U.S. Cl.
   CPC . *A61K 8/97* (2013.01); *A61Q 19/08* (2013.01); *A61K 2800/522* (2013.01); *A61Q 19/004* (2013.01)

(58) Field of Classification Search
   CPC ................. A61K 8/97; A61Q 19/08
   See application file for complete search history.

(56) References Cited

U.S. PATENT DOCUMENTS

2003/0104079 A1*  6/2003  Sakanaka et al. ............ 424/728
2011/0097310 A1   4/2011  Jang et al.

FOREIGN PATENT DOCUMENTS

| KR | 1000255800000 | 2/1988 |
| KR | 1000255820000 | 2/1998 |
| KR | 1020000031530 | 6/2000 |
| KR | 1020020055483 A | 7/2002 |
| KR | 100361433 | 11/2002 |
| WO | 2007052876 A1 | 5/2007 |

OTHER PUBLICATIONS

Wu et al., Production of ginseng and its bioactive components in plant cell culture: Current technological and applied aspects, Journal of Biotechnology, 1999, pp. 89-99, vol. 68(2-3).

Teng, W.L., et al.; "Explant preparation affects culture initiation and regeneration of *Panax ginseng and Panax guinguefolius*," Tissue and Organ Culture, 2002, pp. 233-239, vol. 68.

Lian, et al., "Effect of Plant Growth Regulators and Medium Composition on Cell Growth and Saponin Production during Cell-Suspension Culture of Mountain Ginseng (Panax ginseng C.A. Mayer)," Journal of Plant Biology, Dec. 2002, pp. 201-206, vol. 45.

Han, et al., "Induction of Adventitious Roots and Analysis of Ginsenoside Content and the Genes INvolved in Triterpene Biosynthesis in *Panax ginseng*," Journal of Plant Biology, Feb. 2006, pp. 26-33, vol. 49.

* cited by examiner

*Primary Examiner* — Robert Yamasaki
(74) *Attorney, Agent, or Firm* — Tristan A. Fuierer; Moore & Van Allen, PLLC (57) ABSTRACT

The present invention relates to an anti-aging or antioxidant composition which contains, as an active ingredient, a plant stem cell line derived from the cambium of *Panax ginseng*, including wild ginseng and ginseng, or an extract thereof, a lysate thereof and a culture thereof. The composition has minimized side effects compared to existing anti-aging agents and antioxidants, and thus is safe for the skin. Also, the composition of the present invention shows an antioxidant effect of inhibiting reactive oxygen species caused by exposure to UV radiation that is the major cause of skin aging, and it can effectively reduce or inhibit aging-related factors. Thus, the composition is useful for the prevention and inhibition of aging.

9 Claims, 7 Drawing Sheets

COMPOSITION FOR ANTI-AGING OR ANTIOXIDANT COMPOSITION CONTAINING PLANT STEM CELL LINE DERIVED FROM CAMBIUM OR *PANAX GINSENG* INCLUDING WILD GINSENG AND GINSENG AS ACTIVE COMPONENTS

CROSS REFERENCE TO RELATED APPLICATIONS

This application is a continuation application of and claims the priority of U.S. patent application Ser. No. 12/997,858 filed on Jan. 13, 2011, entitled "ANTI-AGING OR ANTI-OXIDANT COMPOSITION CONTAINING PLANT STEM CELL LINE DERIVED FROM CAMBIUM OF *PANAX GINSENG*" in the name of Mi Ok Jang, et al., which claims priority of International Patent Application No. PCT/KR2009/003176 filed on 12 Jun. 2009, which claims priority of Korean Patent Application No. 10-2008-0056008 filed on 13 Jun. 2008, all of which are hereby incorporated by reference herein in their entireties.

TECHNICAL FIELD

The present invention relates to an anti-aging or antioxidant composition containing, as an active ingredient, any one or more of a cell line derived from the cambium of *Panax ginseng*, including wild ginseng and ginseng, an extract thereof, a lysate thereof and a culture thereof.

BACKGROUND ART

There are about 300,000 species of plants in the world today, and it is known that plants contain useful components exhibiting various physiological activities. The useful components are secondary metabolites that are produced secondarily during normal metabolic processes and accumulated at intracellular specific sites. These useful components are receiving increasing attention, because they serve to defend plants from microorganisms or external animals from biochemical and ecological viewpoint and are advantageous in terms of physiological activity. Secondary metabolites that are produced by plants include alkaloids, flavonoids, carotenoids, glycosides, terpenoids, etc.

Many of such secondary metabolites exhibit moisturizing, skin soothing and toning, UV shielding, whitening, keratin removal, anti-aging, antioxidant, wrinkle reducing, antibacterial, anti-inflammatory and anticancer effects, etc. Accordingly, various cosmetic products containing useful components derived from plants have been developed. For examples, cosmetic products containing useful components derived from plants include: a whitening cosmetic composition containing mulberrin isolated from *Morus alba* (Korean Patent Registration No. 25582), a cosmetic composition containing *Alpinia Katsumadai* extract (Korean Patent Registration No. 295875), a cosmetic composition for preventing skin aging containing ginseng extract (Korean Patent Registration No. 361433), and a cosmetic composition for reducing wrinkles containing *Ecklonia Cava* (Korean Patent Registration No. 2001-25580). In addition, various cosmetic products have been developed which contain extracts of various plants, including chestnut bark, *Xanthii fructus*, gourd, *Caesapinia sappan* L., Giant knotweed, mallow, peppermint, *Alnus japonica*, herb, Birch, *Pora cocos*, Pomegranate, Willow bark, mung beans, rose, etc. Such useful components derived from plants are secondary metabolites which are extracted directly from plants, because the biosynthetic pathways thereof are complex.

Meanwhile, the skin is a primary defense barrier of the human body, which functions to protect various organs in the body from changes in temperature and humidity, and external environmental stimuli such as UV and pollutants, and plays an important role in maintaining homeostasis in vivo. However, UV light, excessive physical and chemical stimuli from the external environment, stresses, nutritional deficiency and the like deteriorate the normal function of the skin and accelerate skin aging phenomena such as firmness loss, keratinization and wrinkle formation and the like. To prevent such phenomena and to keep the skin more healthy and elastic, there have been efforts to use cosmetics containing physiologically active substances obtained from various animals, plants and microorganisms, so as to maintain the intrinsic function of the skin and activate skin cells, thus effectively suppressing skin aging. However, cosmetic raw materials according to the prior art have various problems in that they mostly have insufficient effects or cause skin side effects.

Accordingly, the present inventors have made many efforts to develop natural material-derived compositions which have minimized side effects compared to existing anti-aging agents and antioxidants and have excellent anti-aging and antioxidant effects. As a result, the present inventors have found that a homogeneous cell line derived from the cambium of *Panax ginseng*, a lysate thereof, an extract thereof or a culture thereof have excellent inhibitory effects against aging and oxidation, thereby completing the present invention.

DISCLOSURE OF INVENTION

It is an object of the present invention to a natural material-derived composition which has minimized side effects compared to existing anti-aging agents and antioxidants and shows anti-aging and antioxidant activities.

To achieve the above-object, the present invention provides an anti-aging or antioxidant composition containing any one or more of a cell line, which is derived from the cambium of *Panax ginseng* and has the following characteristics, an extract thereof, a lysate thereof and a culture thereof:

(a) it is in an innately undifferentiated state;
(b) it is a homogeneous cell line; and
(c) it is morphologically characterized by a number of vacuoles.

The present invention also provides an anti-aging cosmetic composition containing any one or more of said cell line, an extract thereof, a lysate thereof and a culture thereof.

The present invention also provides an anti-aging or antioxidant functional food containing any one or more of said cell line, an extract thereof, a lysate thereof and a culture thereof.

Other features and embodiments of the present invention will be more fully apparent from the following detailed description and appended claims.

BRIEF DESCRIPTION OF THE DRAWINGS

FIG. 2 is a graphic diagram showing the results of treating normal human skin fibroblasts (NHF) with various concentrations of an extract of a wild ginseng cambium-derived homogenous cell line of the present invention or a culture medium of the cell line and examining whether the extract or culture medium of the cell line is cytotoxic for the fibroblasts. In FIG. 2, wet: wet cells of ginseng, dry: dry cells of ginseng, media: cultured medium of ginseng cells, E1: elicitation-1 stage, E2: elicitation-2 stage, and G: growth stage.

In FIG. 3, wet: wet cells of ginseng, dry: dry cells of ginseng, media: cultured medium of ginseng cells, E1: elicitation-1 stage, E2: elicitation-2 stage, and G: growth stage.

FIG. 4 is a graphic diagram showing the results of treating normal human skin fibroblasts (NHF) with various concentrations of an extract of a wild ginseng cambium-derived homogenous cell line or a culture medium of the cell line, treating the fibroblasts with UVB radiation, and examining whether an increase in MMP-1 expression caused by UVB radiation is inhibited by the wild ginseng cambium-derived homogenous cell line extract or culture medium. In FIG. 4, wet: wet cells of ginseng, dry: dry cells of ginseng, media: cultured medium of ginseng cells, E1: elicitation-1 stage, E2: elicitation-2 stage, G: growth stage, and RA: retinoic acid.

FIG. 5 is a graphic diagram showing the results of treating normal human skin fibroblasts (NHF) with various concentrations of an extract of a wild ginseng cambium-derived homogenous cell line or a culture medium of the cell line, treating the fibroblasts with UVB radiation, and examining whether an increase in reactive oxygen caused by UVB radiation is inhibited by the wild ginseng cambium-derived homogenous cell line extract or culture medium. In FIG. 5, wet: wet cells of ginseng, dry: dry cells of ginseng, media: cultured medium of ginseng cells, E1: elicitation-1 stage, E2: elicitation-2 stage, G: growth stage, and RA: retinoic acid.

BEST MODE FOR CARRYING OUT THE INVENTION

Unless otherwise defined, all technical and scientific terms used herein have the same meaning as commonly understood by one of ordinary skill in the art. Generally, the nomenclature used herein are well known and conventionally used in the art.

The definition of main terms used in the detailed description of the invention is as follows.

As used herein, the term "cambium" refers to a tissue that thickens the stem and root to allow the plant to grow volumetrically. It was reported that when the cambium, a meristem where the most active cell division occurs, is used as an explant for plant tissue culture, rapid and mass production of cells is possible (Korean Patent Registration No. 10-0533120).

As used herein, the term "lysate" refers to a cell lysate obtained by disrupting cells through a chemical method with, for example, a detergent, or a physical method. The term "extract" of a cell line refers to a substance obtained by dissolving cells in a solvent and isolating the substance, and the extract can be concentrated through distillation or evaporation. Also, the term "culture medium" of the cell line refers to a cell medium from which cells have been removed after culturing the cells. In addition, the term "culture" of the cell line as used herein refers to a material containing a culture medium and/or a cultured cell line, wherein the cultured cell line is intended to include a cell line which differentiates under culture conditions or which have improved ability to produce and/or secrete useful substances.

As used herein, the term "innately undifferentiated" means that cells are not present in an undifferentiated state through a dedifferentiation process, but are originally maintained in a pre-differentiated state.

In one aspect, the present invention provides an anti-aging or antioxidant composition containing, as an active ingredient, any one or more of a cell line derived from the cambium of *Panax ginseng*, a lysate thereof, an extract thereof and a culture thereof. In the present invention, *Panax ginseng* includes wild ginseng or ginseng (Lian M. L. et al., *J. Plant Biology*, 45: 201, 2002; Han J. Y. et al., *J. Plant Biology*, 49:26, 2006; Teng W. L. et al., *Tissue and Organ Culture*, 68:233, 2002). In the present invention, the wild ginseng or ginseng includes outdoor-cultivated ginseng or tissue-cultured ginseng (adventitious root and adventitious root-derived cell line).

The *Panax ginseng* cambium-derived cell line according to the present invention has the following characteristics: (a) it is in an innately undifferentiated state; (b) it is a homogeneous cell line; and (c) it is morphologically characterized by a number of vacuoles. The *Panax ginseng* cambium-derived cell line according to the present invention is additionally characterized in that: (a) it is present as single cells during suspension culture; (b) it has low sensitivity to shear stress in a bioreactor compared to cell lines derived from tissues other than the cambium of *Panax ginseng*, and (c) it has a higher growth rate than those of cell lines derived from tissues other than the cambium of *Panax ginseng* and is cultured stably.

The cell line according to the present invention is obtained using an isolation method comprising the steps of: (a) obtaining storage root tissue containing the cambium of *Panax ginseng*; (b) applying osmotic stress to the obtained cambium-containing storage root tissue, and then culturing the cambium-containing storage root tissue in a IAA (Indole-3-acetic acid)- or IBA (Indole-3-butyric acid)-containing medium, thereby inducing a cambium-derived cell line; and (c) collecting the induced cambium-derived cell line.

In step (b) of the inventive method, the application of osmotic stress is carried out in order to induce the cell line specifically in the cambium. Preferably, it is carried out before culturing the tissue in the IAA- or IBA-containing medium, such that general tissues (i.e., cortex, phloem, xylem and pith) other than the cambium lose the ability to divide, and thus become necrotic when they are treated with a cambial division-specific hormone such as IAA or IBA. Herein, preferably, the osmotic agent is used in an amount of 0.5-2M, and the osmotic stress is applied in a cold state or at room temperature for 16-24 hours, and then removed. However, the scope of the present invention is not limited thereto, because the concentration, treatment time and temperature of the osmotic agent may vary depending on the kind of plant and the state of tissue. In step (b), the IAA or IBA is preferably contained in an amount of 0.1~5 mg/l.

Preferably, step (c) is carried out by proliferating the induced cambium-derived cell line in a medium containing one or more of 2,4-D (2,4-dichlorophenoxyacetic acid), picloram and IBA, and then collecting the cambium-derived cell line. Herein, any one of 2,4-D, picloram and IBA is preferably contained in an amount of 1-5 mg/L, and more preferably 2 mg/L.

In the present invention, the culture of the cell line is preferably obtained by additionally culturing the cell line in a medium, which, as elicitors, contains 3-5 wt % of raw sugar or sugar, and/or any one or more of methyl jasmonate, chitosan, phenylalanin, benzoic acid, ABA, salicylic acid and sodium acetate. Herein, the medium preferably contains 3-5 wt % of raw sugar or sugar; and at least one substance selected from the group consisting of methyl jasmonate, fungal extract, bacterial extract, yeast extract, chitosan, glucomannan, glucan, phenylalanine, benzoic acid, salicylic acid, arachidonic acid, STS, mevalonalonate N-benzolyglycine, ABA, SNP, IPP, BHT, CCC, ethephon, hippuric acid, ammonium ceric nitrate, $AgNO_3$, vanadyl sulfate, p-aminobenzoic acid, brassinosteroids, sodium alginate, and sodium acetate.

Also, in the present invention, it is possible to use a culture obtained by treating the cell line with elicitors, including UV radiation, heat, ethylene, an antifungal agent, an antibiotic, heavy metal salt and high-concentration salt, to apply physical and chemical stresses thereto.

The medium used in the present invention is a conventional medium for plant tissue culture, and examples thereof include, but are not limited to, N6 medium, SH medium, MS medium, AA medium, LS medium, B5 medium, WPM medium, LP medium, White medium, GD medium, DKW medium, DCR medium, etc.

In the present invention, the extract is preferably obtained using a solvent selected from the group consisting of distilled water, alcohol, acetone, DMSO (dimethyl sulfoxide), and mixed solvents thereof. Herein, examples of the alcohol include alcohols having 1 to 5 carbon atoms, such as methanol and ethanol.

In the present invention, the extract may be obtained by fractionating the cell line sequentially with distilled water, methanol and acetone.

In one Example of the present invention, fibroblasts that synthesize collagen (the primary component of the skin dermis) were treated with said cell line extract or culture medium and, as a result, it was found that the cell line extract and culture medium have an excellent effect on the proliferation of fibroblasts, suggesting that the cell line extract and culture medium of the present invention have the effect of increasing skin elasticity. In another Example of the present invention, it was found that the cell line extract and culture medium of the present invention have the effect of inhibiting the expression of MMP-1 which degrades skin collagen to form skin wrinkles, suggesting that they have the effect of preventing and reducing wrinkles. In still another Example of the present invention, it was found that the cell line extract and culture medium of the present invention have the effect of inhibiting reactive oxygen species induced by UV radiation, suggesting that they have an antioxidant effect. Because it is widely known to those of ordinary skill in the art that compositions having antioxidant activity have an anti-aging effect, it is obvious that the composition according to the present invention has an anti-aging effect.

In still another Example of the present invention, in order to ensure objectivity, anti-aging and antioxidant tests for the cell line extract and culture medium of the present invention were performed by an external analysis organization. As a result, it was found that the cell line extract and culture medium of the present invention have a very excellent anti-aging effect compared to RA which is known to have an excellent anti-aging effect and wild ginseng extract. In addition, it could be seen that the cell line extract and culture medium of the present invention have a much more antioxidant effect compared to an extract of outdoor-cultivated wild ginseng.

Accordingly, it was found as described above that the cell line extract had an anti-aging effect and antioxidant activity. Thus, even though in the present invention, there is no specific example showing that the composition containing the cell line shows an anti-aging effect and antioxidant activity, it will be obvious to those skilled in the art that the composition containing the cell line according to the present invention or a lysate thereof can also show an anti-aging effect and antioxidant activity.

An anti-aging or antioxidant composition containing any one or more of the cell line according to the present invention, an extract thereof, a lysate thereof and a culture thereof may be provided as a pharmaceutical composition containing any one or more of said cell line, a lysate thereof, an extract thereof and a culture thereof alone or in combination with at least one pharmaceutically acceptable carrier, excipient or diluent. The cell line, a lysate thereof, an extract thereof or a culture medium thereof may be contained in a pharmaceutical composition in a pharmaceutically effective amount depending on disease and its severity, the patient's age, weight, health condition and sex, the route of administration and the period of treatment.

As used herein, the term "pharmaceutically acceptable composition" refers to a composition that is physiologically acceptable and does not cause allergic reactions or similar reactions such as gastrointestinal disorder or vertigo, when administered to humans. Examples of said carrier, excipient or diluent may include lactose, dextrose, sucrose, sorbitol, mannitol, xylitol, erythritol, maltitol, starch, acacia rubber, alginate, gelatin, calcium phosphate, calcium silicate, cellulose, methyl cellulose, polyvinylpyrrolidone, water, methylhydroxybenzoate, propylhydroxybenzoate, magnesium stearate and mineral oils.

The pharmaceutical composition may additionally contain fillers, anti-aggregating agents, lubricants, wetting agents, perfumes, emulsifiers and preservatives. Also, the pharmaceutical composition of the present invention may be formulated using a method well known in the art, such that it can provide the rapid, sustained or delayed release of the active ingredient after administration to mammals. The formulation may be in the form of powders, granules, tablets, emulsions, syrups, aerosols, soft or hard gelatin capsules, sterile injection solutions, sterile powders, etc.

In another aspect, the present invention relates to an anti-aging cosmetic composition containing, as an active ingredient, any one or more of said *Panax ginseng* cambium-derived cell line, a lysate thereof, an extract thereof and a culture thereof.

As used herein, the term "functional cosmetic product" refers to a cosmetic product, the functionality of which has been improved by adding thereto any one or more of the cell line according to the present invention, an extract thereof, a lysate thereof and a culture medium thereof. For example, the anti-aging cosmetic composition containing the cell line of the present invention, a lysate thereof, an extract thereof or a culture medium thereof may be used to prepare a functional cosmetic product.

The cosmetic composition of the present invention may contain conventional ingredients for cosmetics, in addition to the cell line or its lysate, extract or culture medium as an active ingredient. For example, the cosmetic composition may contain conventional auxiliaries such as antioxidants, stabilizers, solubilizing agents, vitamins, pigments and perfumes, as well as carriers.

The cosmetic composition of the present invention may be prepared into any formulations that are conventional in the art. Preferably, the cosmetic composition can be prepared into a formulation selected from the group consisting of skin lotion, milk lotion, nourishing cream, massage cream, nourishing essence, pack, makeup base, foundation, body oil, hair oil, shampoo, and rinse.

The cosmetic composition of the present invention, which contains any one or more of the cell line of the present invention, an extract thereof, a lysate thereof and a culture thereof, has an antioxidant effect, and thus has the effects of eliminating free radicals generated in the skin and protecting intracellular antioxidant systems. Accordingly, the cosmetic composition of the present invention can exhibit the effects of preventing and delaying skin aging resulting from oxidation caused by the action of, for example, free radicals.

In another aspect, the present invention relates to an anti-aging or antioxidant functional food containing, as an active ingredient, any one or more of the *Panax ginseng* cambium-derived cell line, a lysate thereof, an extract thereof and a culture thereof.

As used herein, the term "functional food" refers to a food, the functionality of which has been improved by adding thereto the cell line of the present invention, a lysate thereof, an extract thereof or a culture medium thereof.

EXAMPLES

Hereinafter, the present invention will be described in further detail with reference to examples. It is to be understood, however, that these examples are for illustrative purposes only and are not to be construed to limit the scope of the present invention.

Particularly, although the skin anti-aging effects of an extract and culture medium of a *Panax ginseng* cambium-derived cell line were confirmed in the following examples, it will be obvious to those skilled in the art that the use of the cell line or its lysate can provide the same results as those obtained using the extract or culture medium of the cell line.

Example 1

Preparation of Cell Line Derived from Cambium of Wild Ginseng 1-1: Preparation of Plant Material "A" of FIG. 1(*a*) shows the typical feature of wild ginseng used in the present invention. In order to use the main root of purchased wild ginseng, the main root was purchased, and then washed with running water to remove earth or other contaminants from the surface thereof, and the surface of the main root was washed with a liquid detergent. Then, the main root was allowed to stand under running water. The washed root tissue was placed in a sterilized flask in a clean bench and disinfected with 70% ethanol for a time ranging from about 30 seconds to about 1 minute. Then, it was rinsed with sterile water and treated with a disinfectant solution containing 1-1.5% sodium hypochlorite (Junsei, Japan) for about 5-15 minutes. At this time, in order to allow the disinfectant solution to effectively penetrate into the tissue, several drops of TWEEN 20 (polyoxyethylenesorbitan monolaurate, Junsei, Japan) were added to the tissue. Following this, the tissue was rinsed 3-5 times with sterile water. In order to prevent browning of the disinfected tissue, the disinfected main root was placed in antioxidant-containing BIM (browning inhibition medium) and shake-cultured for about 30 minutes to 1 hour. The cultured tissue was placed on sterile filter paper to remove water.

The composition of BIM used and the concentrations of components thereof are shown in Table 1 below.

TABLE 1

Composition of BIM and concentrations of components thereof

| Composition | Concentrations |
|---|---|
| McCown WPM salt | ¼ strength |
| Sucrose | 1% (w/v) |
| PVP(polyvinyl pyrrolidone) | 0.5% (w/v) |
| Ascorbic acid | 100 mg/l |
| Citric acid | 150 mg/l |
| Adjust to pH 5.8 | |

In Table 1, the salt is added in an amount corresponding to the total volume of BIM.

In order to prevent the above treated material from browning, the material was placed in a dish containing an antioxidant-containing CS solution (cutting solution, Table 2) and peeled. Then, the material was cut into two equal parts, and each of the parts was cut to a size of 0.5-0.7 cm (width)×0.5-0.7 cm (length)×0.2-0.5 mm (thickness) in such a manner that each cut portion contained a cambium portion having active division ability. "B" of FIG. 1(*a*) shows the explant prepared by cutting the main root of the wild ginseng to the above size in such a manner that the explant contains the cambium.

TABLE 2

CS (cutting solution)

| Component | Concentration |
|---|---|
| PVP (Polyvinyl pyrrolidone) | 0.5% (w/v) |
| Ascorbic acid | 100 mg/l |
| Citric acid | 150 mg/l |

1-2: Treatment of Explant Containing Cambium of Main Root of Wild Ginseng with Osmotic Agent The explant prepared in Example 1-1 was treated with osmotic stress in order to necrotize differentiated tissues (i.e., phloem, xylem, pith, etc.) and to allow only the meristem cambium to survive. The cambium-containing explant was blotted onto a preculture medium (medium 1, Table 3) having filter paper laid thereon, and it was placed in a flask containing 1M sucrose solution (Duchefa, Netherland) and was treated with osmotic stress in a cold state for 16-24 hours. Then, the explant was treated in 0.05M sucrose solution for 5 minutes and in 0.1M sucrose solution for 5 minutes to remove the stress caused by the high-concentration sucrose. The cambium-containing explant from which the osmotic stress has been removed was placed on a preculture medium (medium 1) having filter paper laid thereon to remove moisture.

TABLE 3

Composition of preculture medium (medium 1)

| Composition | | mM | mg/l |
|---|---|---|---|
| Macroelements | Ca(NO$_3$)$_2$ | 2.35 | 471.26 |
| | NH$_4$NO$_3$ | 5 | 400 |
| | MgSO$_4$•7H$_2$O | 1.5 | 180.54 |
| | K$_2$SO$_4$ | 5.68 | 990 |
| | CaCl$_2$•2H$_2$O | 0.65 | 72.5 |
| | KH$_2$PO$_4$ | 1.25 | 170 |
| | | μM | |
| Microelements | MnSO$_4$•4H$_2$O | 131.94 | 22.3 |
| | ZnSO$_4$•7H$_2$O | 29.91 | 8.6 |
| | Na$_2$MoO$_4$•2H$_2$O | 1.03 | 0.25 |
| | H$_3$BO$_3$ | 100.27 | 6.2 |
| | CuSO$_4$•5H$_2$O | 1.0 | 0.25 |
| | FeNa-EDTA | 100 | 36.7 |

TABLE 3-continued

Composition of preculture medium (medium 1)

| | Composition | | mg/l |
|---|---|---|---|
| Vitamin | Glycine | 26.64 | 2.0 |
| | myo-Inositol | 554.94 | 100 |
| | Nicotinic acid | 4.06 | 0.5 |
| | Pyridoxine-HCl | 2.43 | 0.5 |
| | Thiamine-HCl | 2.96 | 1.0 |

1-3: Induction of Cambium-Derived Homogeneous Cell Line in Explant Containing the Cambium of Wild Ginseng In order to induce a cambium-derived homogeneous cell line having the cell division ability, the explant treated with osmotic stress in Example 1-2 was transferred to a cell line induction medium (medium 2, Table 4). The composition of the medium used is shown in Table 4 below. The transferred explant was cultured in a dark condition at 22±1° C.

TABLE 4

Medium composition (medium 2) used to induce cambium-derived homogeneous cell line

| Component | Concentration and condition |
|---|---|
| Salt | Full strength WPM |
| Sucrose | 3% (w/v) |
| IAA(Indole-3-acetic acid) | 2 mg/l |
| pH | 5.8 |
| Gelrite | 0.3% (w/v) |
| Ascorbic acid | 100 mg/l |
| Citric acid | 150 mg/l |

As shown in Table 5 below, in the explants transferred directly onto the homogeneous cell line-induction medium without carrying out osmotic treatment, a yellow color reaction was shown with respect to the cambium at an initial stage (2-3 days) after the transfer, and then with the passage of time, the entire explant turned yellow. The explant which has showed the yellow color reaction with respect to the cambium was subcultured in an optimal medium (medium 3) for the isolation and proliferation of a cambium-derived cell line in order to induce and proliferate the cambium-derived cell line, but the browning phenomenon became severe, and any reaction other than the browning color reaction was not shown even with the passage of time.

Figure 1:
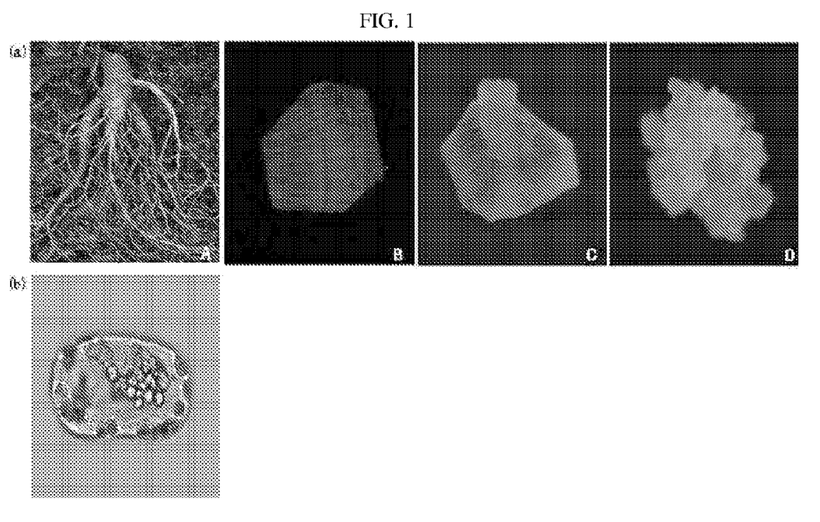
FIG. 1 is a set of photographs showing a process of deriving a cell line according to the present invention, and a cell line derived from the cambium of wild ginseng.

However, after the osmotic stress was treated and removed, it was observed as shown in Table 5 that, in the explant inoculated onto the homogeneous cell line-induction medium, a homogeneous cell line was specifically induced only in the cambium without being induced in other tissues. Specifically, it was observed that, in the transferred explant which has been treated with osmotic stress and from which the osmotic stress has been released, the cambium of the explant started to turn a light yellow after 3-7 days of the culture, and after about 7-14 days therefrom, a round cell line was induced at the portion that changed to the light yellow color. "C" of FIG. 1(a) shows that the homogeneous cell line having cambium-specific division ability was induced in the explant containing the cambium of wild ginseng.

Meanwhile, the explant was cultured in a 2,4-D-containing medium, which was not the homogeneous cell line-induction medium and has been used in the conventional culture of Panax ginseng, including ginseng and wild ginseng. In this case, it was observed that the entire explant started to turn yellow after 7-10 days of the culture, and about 7-14 days therefrom, cells were induced throughout the whole cross section.

TABLE 5

Comparison of reaction between explant treated with osmotic stress and explant not treated with osmotic stress

| Treatment | Not treated | Treated for 16 hours | Treated for 20 hours | Treated for 24 hours |
|---|---|---|---|---|
| Aspect | A yellow color reaction progressed respect to the cambium with respect to the cambium at the initial induced stage after the inoculation, while this reaction spread throughout the explant. Then, a severe browning color reaction progressed throughout the explants including the cambium, and the induction of a homogeneous cell line, specific in the cambium, was no longer shown. | It was observed that cells were specifically induced only in the cambium. When the explant was treated with osmotic stress for varying periods of time, similar results were shown. In other words, there was no significant difference between the treatment periods. | | |

1-4: Proliferation of Isolated Homogeneous Cell Line Derived from Cambium of Wild Ginseng The cambium-derived homogeneous cell line having the ability to divide, induced in Example 1-3, was allowed to proliferate. The medium used in the proliferation was an optimal medium (Table 7) for proliferation of the cambium-derived homogeneous cell line having to the ability to divide, which contained a basal salt composition (Table 6).

TABLE 6

Basal salt composition of optimal medium for the isolation and proliferation of cambium-derived homogeneous cell line having the ability to divide

| | Composition | | mg/L |
|---|---|---|---|
| | | mM | |
| Macroelements | $CaCl_2 \cdot 2H_2O$ | 2.99 | 332.02 |
| | $KH_2PO_4$ | 1.25 | 170 |
| | $KNO_3$ | 18.79 | 1900 |
| | $MgSO_4$ | 1.5 | 180.54 |
| | $NH_4NO_3$ | 20.61 | 1650 |
| | | uM | |
| Microelements | $CoCl_2 \cdot 6H_2O$ | 0.11 | 0.025 |
| | $CuSO_4 \cdot 5H_2O$ | 0.1 | 0.025 |
| | FeNa-EDTA | 100 | 36.7 |
| | $H_3BO_3$ | 100.27 | 6.2 |
| | KI | 5.0 | 0.83 |
| | $MnSO_4 \cdot 4H_2O$ | 100 | 16.9 |
| | $Na_2MoO_4 \cdot 2H_2O$ | 1.03 | 0.25 |
| | $ZnSO_4 \cdot 7H_2O$ | 29.91 | 8.6 |
| Vitamins | Glycine | 26.64 | 2.0 |
| | myo-Inositol | 554.94 | 100 |
| | Nicotinic acid | 4.06 | 0.5 |
| | Pyridoxine-HCl | 2.43 | 0.5 |
| | Thiamine-HCl | 0.3 | 0.1 |

TABLE 7 composition of optimal medium (medium) for the isolation and proliferation of cambium-derived homogeneous cell line having the ability to divide

| Component | Concentration and condition |
|---|---|
| Salt | Full strength MS |
| Sucrose | 3% (w/v) |
| 2,4-D(2,4-dichlorophenoxyacetic acid) | 2 mg/L |

TABLE 7-continued composition of optimal medium (medium) for
the isolation and proliferation of cambium-derived
homogeneous cell line having the ability to divide

| Component | Concentration and condition |
| --- | --- |
| pH | 5.8 |
| Gelrite | 0.3% (w/v) |
| Ascorbic acid | 100 mg/L |
| Citric acid | 150 mg/L |

As shown in "C" of FIG. 1(a), after the homogeneous cell line has been was specifically induced only in the cambium using osmotic stress treatment and medium 2, the homogeneous cell line was subcultured in medium 3 as shown in Table 7. As a result, the cambium-derived homogeneous cell line having the ability to divide continually divided and proliferated, and thus after about 10-20 days of the culture, the cambium-derived homogeneous cell line having the ability to divide could be isolated. The wild ginseng cambium-derived homogeneous cell line thus isolated was allowed to proliferate again by culturing it in the same medium. "D" of FIG. 1(a) shows that the isolated cambium-specific homogeneous cell line was allowed to proliferate in medium 3.

1-5: Observation of Characteristics of Isolated Cell Line

The wild ginseng cambium-derived homogeneous cell line was placed in a flask containing the liquid medium shown in Table 8. Then, the cell line was cultured in a rotating shaker at 100 rpm in a dark condition at 25±1° C. Herein, the subculture interval was set to 2 weeks, such that the cultured cells could always maintain high vitality in the exponential growth phase. Meanwhile, the ginseng cotyledon-derived callus was also cultured in medium 4 of Table 8, and the cultured callus was compared with the wild ginseng cambium-derived homogeneous cell line of the present invention.

TABLE 8

Suspension medium for Panax ginseng (medium 4)

| Component | Concentration and condition |
| --- | --- |
| Salt | Full strength MS |
| Sucrose | 3% (w/v) |
| 2,4-D(2,4-dichlorophenoxyacetic acid) | 2 mg/L |
| pH | 5.8 |

The quantification of cell aggregation was observed under an optical microscope (biological microscope CX31, Olympus, Japan) and, as a result, it could be seen that, as shown in Table 9 below, more than 90% of cells of the cell lines according to the present invention were present as single cells during suspension culture. As shown in FIG. 1(b), it could be observed that the cell line of the present invention was morphologically characterized by a large number of vacuoles and was in an undifferentiated state.

TABLE 9

The type of cell aggregates of Panax ginseng long-term cultures

| Large cell aggregates | Moderate cell aggregates | Small cell aggregates | Single cell population | Explant source |
| --- | --- | --- | --- | --- |
| 90% | 7% | 2% | 1% | cotyledon |
| 0 | 0 | 5% | 95% | cambium |

Large cell aggregates, size higher than $1.5 \times 10^3$ μm;
Moderate cell aggregates $1 \times 10^3$ μm;
Small cell aggregates $4 \times 10^2$ μm < size < $1 \times 10^3$ μm Meanwhile, in order to examine the possibility of scale-up culture, each of the ginseng cotyledon-derived callus and the wild ginseng cambium-derived cell line of the present invention was cultured in an airlift bioreactor (Sung-Won Cytec, Korea) having an internal volume of 3 L. The medium used in the culture was the liquid medium shown in Table 8 and was maintained in a dark condition at 25±1° C.

As a result, as shown in Table 10, the doubling time of the ginseng cotyledon-derived cell culture was 21 days in the flask and 28 days in the reactor. In other words, it was seen that, when cultured in the flask, the cambium-derived cell line according to the present invention showed about 3 to 5-fold higher growth rate compared to cell lines derived from other tissues, and when cultured in the reactor, the cambium-derived cell line according to the present invention showed 5 to 9-fold higher growth rate compared to cell lines derived from tissues other than the cambium. This is believed to be because cell viability of the heterogeneous cell line rapidly decreased due to growth ring production in the reactor, plant cell aggregation during culture, and the sensitivity of hard cell walls to shear stress.

Meanwhile, the doubling time of the cambium-derived cell culture medium according to the present invention in the reactor was 3-4 days, which did not differ from that in the flask or was rather shortened compared to that in the flask. The cambium-derived homogeneous cell culture medium formed a very small growth ring area in the bioreactor, and the ring on the inner wall was simply eliminated, when a simple stimulus was applied to the incubator to shake the medium. Also, it was shown that the cell line of the present invention had low aggregation and contained a large number of vacuoles, and thus had low sensitivity to shear stress, such that cell viability did not decrease. In other words, it was seen that the cambium-derived cell line according to the present invention had low sensitivity to shear stress resulting from shaking in the bioreactor for scale-up culture, and thus could be produced rapidly in large amounts in the bioreactor. Accordingly, it could be seen that the cambium-derived cell line according to the present invention had 5 to 9-fold lower sensitivity to shear stress compared to cell lines derived from tissues other than the cambium.

TABLE 10

Doubling time of wild ginseng cambium-derived cell line and cotyledon-derived cell line in liquid suspension culture and bioreactor

| Explant source | Doubling time (day) | |
| --- | --- | --- |
|  | flask | bioreactor |
| cotyledon | 21 | 28 |
| cambium | 5 | 3~4 |

1-6: Treatment with Elicitor

The cell line, which has been suspension-cultured for 14 days as described in Example 1-5, was divided into three groups for experiments.

In other words, the following cell lines were collected and subjected to subsequent tests: (1) the cell line (growth stage) suspension-cultured for 14 days, (2) a cell line (Elicitation 1), obtained by culturing the 14-day suspension-cultured cell line in a medium (containing sterile water, 3-5 wt % (g/L) raw sugar and 100 μM methyl jasmonate) in a dark condition for 14 days, and (3) a cell line (Elicitation 2), obtained by culturing the 14-day suspension-cultured cell in a medium (containing 100 μM methyl jasmonate) in a dark condition for 14 days.

Example 2

Preparation of Extract of Wild Ginseng Cambium-Derived Cell Line

Active substances were extracted in the following manner from three cell lines prepared in Example 1:

(1) Preparation of DMSO (dimethyl sulfoxide) extract (i) 500 g of each of the cell line, from which the medium has been removed, and the freeze-dried cell line, was dissolved in 500 ml of DMSO with stirring at 50° C. for 6 hours.

(ii) After completion of the dissolution, the cell solution was centrifuged at 3,000 g for 10 minutes, and the supernatant was collected, thus obtaining a DMSO-soluble substance.

(iii) The obtained DMSO-soluble substance was concentrated using a rotary vacuum concentrator.

(iv) The concentrated sample was dried using a freeze dryer, thereby obtaining a DMSO extract.

(2) Preparation of distilled water extract, methanol extract and acetone extract (i) 500 g of each of the cell line, from which the culture medium has been removed, and the freeze-dried cell line, was dissolved in 500 ml of distilled water with stirring at 50° C. for 6 hours.

(ii) After completion of the dissolution, the cell solution was centrifuged at 3,000 g for 10 minutes, and the supernatant was collected, thus obtaining a distilled water-soluble substance.

(iii) After obtaining the distilled water-soluble substance, the remaining distilled water-insoluble substance was dissolved in 500 ml of methanol with stirring at room temperature for 6 hours.

(iv) After completion of the dissolution, the solution was centrifuged at 3,000 g for 10 minutes, and the supernatant was collected, thus obtaining a methanol-soluble substance.

(v) After obtaining the methanol-soluble substance, the remaining methanol-insoluble substance was dissolved in 500 ml of acetone with stirring at room temperature for 6 hours.

(vi) After completion of the dissolution, the solution was centrifuged at 3,000 g for 10 minutes, and the supernatant was collected, thus obtaining an acetone-soluble substance.

(vii) The distilled water-, methanol- and acetone-soluble substances obtained as described above were concentrated using a rotary vacuum evaporator.

(vii) The concentrated samples were dried using a freeze dryer and dissolved in distilled water, methanol and acetone, thereby obtaining a distilled water extract, a methanol extract and an acetone extract.

(3) Preparation of control (i) 500 g of a freeze-dried wild ginseng root was dissolved in 500 ml of DMSO with stirring at 50° C. for 6 hours.

(ii) After the dissolution, the solution was centrifuges at 3,000 g for 10 minutes, and the supernatant was collected, thus obtaining a DMSO-soluble substance.

(iii) The distilled water-soluble substance was concentrated using a rotary vacuum evaporator.

(iv) The concentrated sample was dried using a freeze dryer, thereby obtaining a DMSO extract of wild ginseng as a control.

Example 3

Examination of Cytotoxicity

In order to determine the concentration of sample to be used in tests, a cytotoxicity test was performed in the following manner.

NHF (normal human fibroblast) cells used in the test were isolated from the fetal foreskin and cultured. A medium used in the cell culture was prepared by adding 10% fetal bovine serum (FBS, Hyclone, Logan, Utah, USA), inactivated by heating at 56° C. for 30 minutes, 100 unit/ml penicillin, 100 µg/ml streptomycin and 300 µg/ml-glutamine, to DMEM medium (Invitrogen Gibco life tech. Vienna, Austria). The cells were cultured in the above medium in a 5% $CO_2$ incubator at 37° C. at a relative humidity of 95%, and subcultured at 3 to 4-day intervals immediately before the cells would be fused with each other. The NHF cells were used in the experiments of this Example and Examples 4 and 5 below.

The NHF(p5) cells (normal human fibroblast cells) were dispensed in 96-well plates at a density of 5,000 cells/well, and after 24 hours, were treated with each of the DMSO extracts and culture media of the wild ginseng cambium-derived cell line, prepared in Example 2, at various concentrations (Wet and dry DMSO extracts of the wild ginseng calcium-derived cell line: ppm; and culture media of the cell line: %). Then, the cells were allowed to proliferate. As a control, cells, treated with neither the extract nor the culture medium, were used. Next, WST-1 solution was diluted 100-fold and added to each well of the plate, and after 2 hours, the absorbance of the plate was measured.

Figure 2:
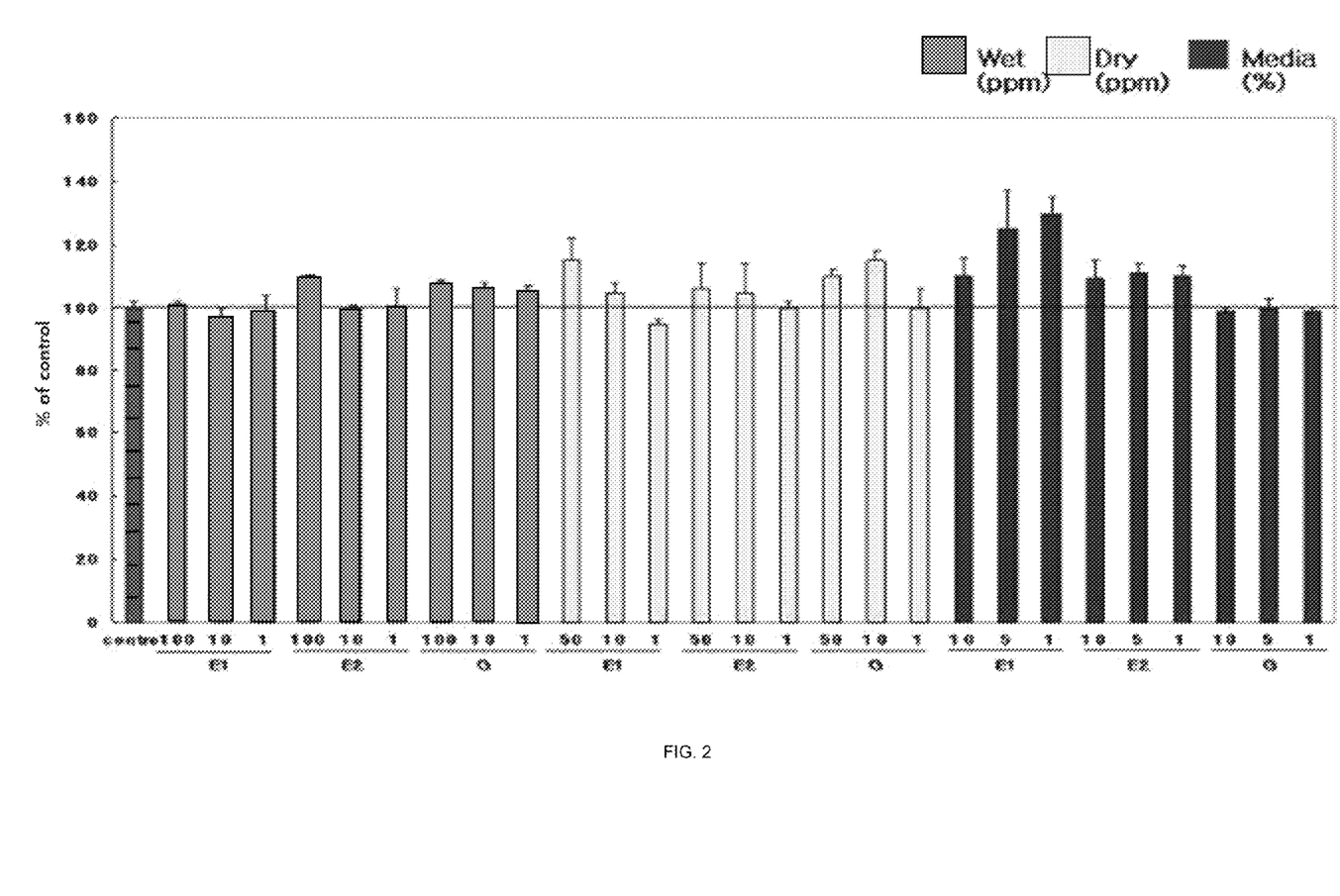

As a result, as shown in Table 11 below and FIG. 2, the extracts and the culture media did not show toxicity in the concentration ranges used in the experiment. Extracts or culture media showing a cell viability of 80% or more were determined to be non-toxic. In Table 11, "Elicitation 1" indicates a DMSO extract of the cell line of Example 1-6, treated with 3-5 wt % (g/L) of raw sugar and 100 µM of methyl jasmonate, "Elicitation 2" indicates a DMSO extract of the cell line of Example 1-6, treated with 100 µM of methyl jasmonate, "Growth" indicates a DMSO extract of the 14-day-suspension-cultured cell line (growth stage) of Example 1-6, and "Media" indicates culture media removed during the preparation of the cell line extracts.

TABLE 11

Examination of cytotoxicity of wild ginseng cambium-derived homogeneous cell line extracts or culture media

| Sample condition | Stage | Concentration (ppm or %) | % of control |
| --- | --- | --- | --- |
| Control | | | 100 |
| Wet (ppm) | Elicitation 1 | 100 | 102 |
| | | 10 | 95 |
| | | 1 | 98 |
| | Elicitation2 | 100 | 110 |
| | | 10 | 100 |
| | | 1 | 98 |
| | Growth | 100 | 108 |
| | | 10 | 106 |
| | | 1 | 105 |
| Dry (ppm) | Elicitation 1 | 50 | 115 |
| | | 10 | 105 |
| | | 1 | 95 |
| | Elicitation2 | 50 | 105 |
| | | 10 | 105 |
| | | 1 | 100 |
| | Growth | 50 | 110 |
| | | 10 | 115 |
| | | 1 | 100 |
| Media (%) | Elicitation 1 | 10 | 110 |
| | | 5 | 125 |
| | | 1 | 135 |
| | Elicitation2 | 10 | 110 |
| | | 5 | 115 |
| | | 1 | 115 |

TABLE 11-continued

Examination of cytotoxicity of wild ginseng
cambium-derived homogeneous cell line extracts or culture media

| Sample condition | Stage | Concentration (ppm or %) | % of control |
|---|---|---|---|
| | Growth | 10 | 98 |
| | | 5 | 100 |
| | | 1 | 98 |

Example 4

Examination of Effect on Proliferation of Fibroblasts—Examination of Anti-Aging Effect Normal human fibroblast cells (NHF cells) cultured in 3.5% FBS-containing DMEM (Doubecco's Modified Eagle's Media) medium were dispensed in a 96-well microtiter plate at density of 5,000 cells/well and starved for 24 hours. Then, the cells were treated for 48 hours with the DMSO extract or culture medium of the wild ginseng cambium-derived cell line, prepared in Example 2, in 0.5% FBS minimal essential media at various concentrations (wet and dry DMSO extracts of the wild ginseng calcium-derived cell line: ppm; and culture media of the cell line: %).

After the cells had been cultured, WST-1 solution was diluted 100-fold and dispersed in the plates, and after 2 hours, 50 μl of 0.2% MTT (3-[4,5-dimethylthiazol-2-yl]-2,5-diphenyl tetrazolium bromide) solution was added to each well of the plate. Then, the cells were cultured at 37° C. for 4 hours, and the produced formazan was dissolved in DMSO (dimethyl sulfoxide). The absorbance of the dissolved formazan was measured at 570 nm using a microplate reader. The test group treated with the wild ginseng cambium-derived cell line extract or culture medium was compared with the control treated with neither the extract nor the culture medium, and the results of the comparison are shown in Table 12 below. In Table 12, "10% FBS" indicates cells cultured in 10% FBS that is a nutrient medium concentration for maximal growth in animal cell culture, and "Control" is a negative control group and indicates cells cultured in 0.5% FBS essential medium without adding the cell line extract or culture medium.

TABLE 12

Effect of wild ginseng cambium-derived homogeneous
cell line extract or culture medium on the proliferation of fibroblasts

| Sample condition | Stage | Concentration (ppm or %) | % of control |
|---|---|---|---|
| Control | | | 100 |
| 10% FBS | | | 145 |
| Wet (ppm) | Elicitation 1 | 100 | 110 |
| | | 10 | 105 |
| | | 1 | 98 |
| | Elicitation 2 | 100 | 115 |
| | | 10 | 110 |
| | | 1 | 113 |
| | Growth | 100 | 125 |
| | | 10 | 115 |
| | | 1 | 110 |
| Dry (ppm) | Elicitation 1 | 50 | 130 |
| | | 10 | 118 |
| | | 1 | 110 |
| | Elicitation 2 | 50 | 120 |
| | | 10 | 115 |
| | | 1 | 112 |

TABLE 12-continued

Effect of wild ginseng cambium-derived homogeneous
cell line extract or culture medium on the proliferation of fibroblasts

| Sample condition | Stage | Concentration (ppm or %) | % of control |
|---|---|---|---|
| | Growth | 50 | 122 |
| | | 10 | 118 |
| | | 1 | 110 |
| Media (%) | Elicitation 1 | 10 | 108 |
| | | 5 | 105 |
| | | 1 | 105 |
| | Elicitation 2 | 10 | 108 |
| | | 5 | 103 |
| | | 1 | 105 |
| | Growth | 10 | 102 |
| | | 5 | 98 |
| | | 1 | 102 |

Figure 3:
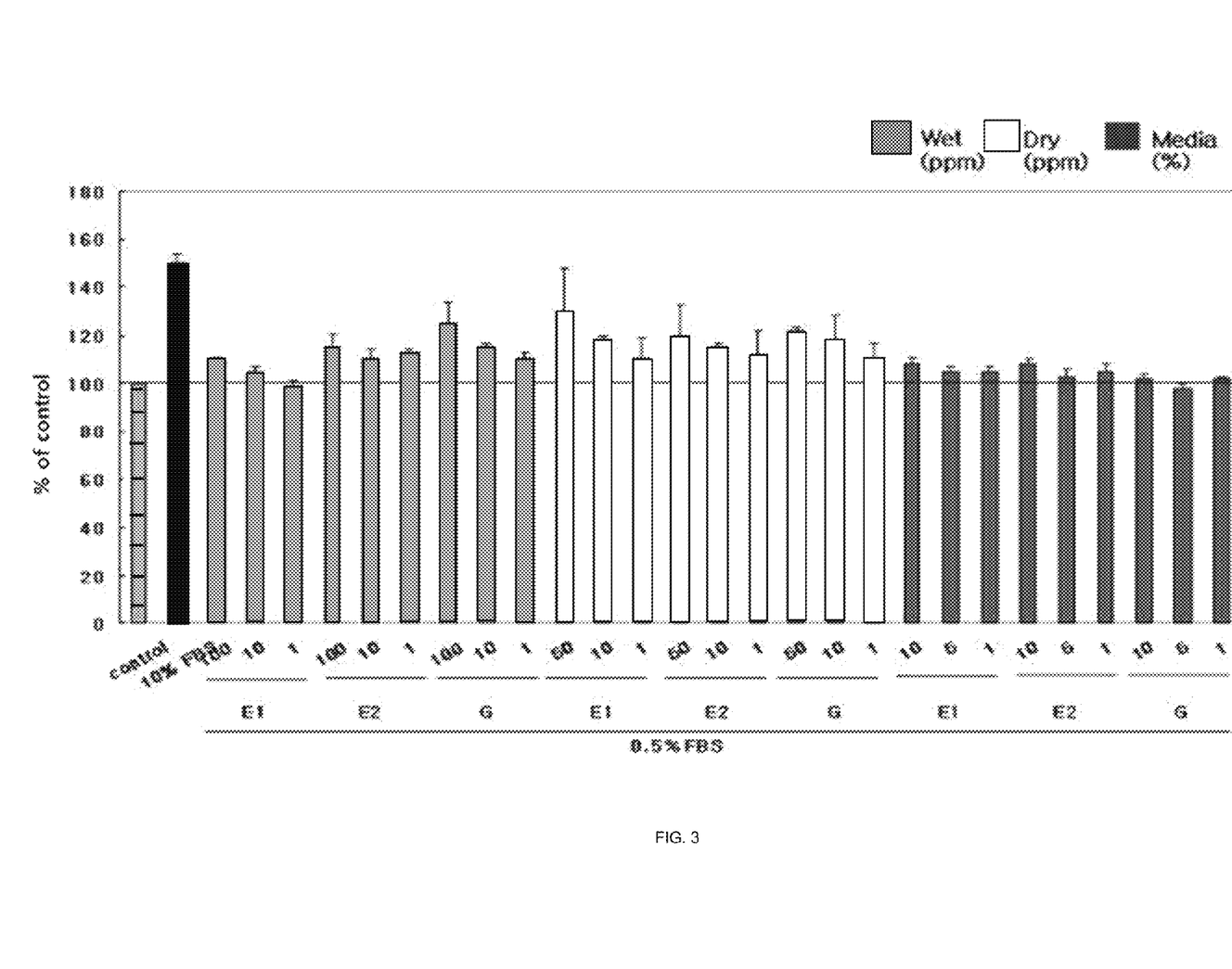
FIG. 3 is a graphic diagram showing the results of treating normal human skin fibroblasts (NHF) with various concentrations of an extract of a wild ginseng cambium-derived homogenous cell line or a culture medium of the cell line, culturing the fibroblasts in 0.5% FBS minimal essential medium, and examining the effect of the wild ginseng cambium-derived homogenous cell line extract or culture medium on the proliferation of the fibroblasts.

As can be seen in Table 12 and FIG. 3, the cell line extract and culture medium according to the present invention had an effect on the proliferation of fibroblasts, unlike the control, and particularly, the freeze-dried cell line extract (Dry) had an excellent effect on the proliferation of fibroblasts.

Also, the freeze-dried cell line extracts (Dry) in various growth stages were compared with each other, the extract of Elicitation 1 had the best effect on the proliferation of fibroblasts, and the cells of Elicitation 2 and the cells of Growth stage showed similar effects in the proliferation of fibroblasts. In other words, it could be found that, because the fibroblasts synthesis collagen (the primary component of the skin dermis), the cell line extract according to the present invention has the effect of increasing skin elasticity.

Example 5

Examination of Effect of Inhibiting MMP-1 Expression Caused by UV Radiation—Examination of Anti-Aging Effect When MMPs are increased due to exposure to UV radiation, the increased MMPs will degrade skin collagen to form skin wrinkles. Thus, in order to examine whether MMP-1 expression that increased due to UV radiation is inhibited by the extract or culture medium of the wild ginseng cambium-derived homogeneous cell line, the following test was carried out.

NHF(p6) cells were dispensed in a 12-well plate at a density of 75,000 cells/well and starved for 24 hours. Then, the cells were radiated with 40 mJ of UVB and treated with varying concentrations of each of the samples for 48 hours. Then, an experiment was carried out using a kit (Amersham, RPN 2610). As a positive control, 10 μM retinoic acid was used

TABLE 13

Inhibitory effects of wild ginseng cambium-
derived homogeneous cell line extract or culture medium on
MMP-1 expression caused by UV radiation

| Sample | Stage | Concentration (ppm or %) | % of control |
|---|---|---|---|
| No UV | | | 100 |
| Control UV | | | 230 |
| Retinoic acid | | 10 uM | 85 |
| Wet (ppm) | Elicitation 1 | 100 | 125 |
| | | 10 | 130 |
| | Elicitation2 | 100 | 125 |
| | | 10 | 135 |

TABLE 13-continued

Inhibitory effects of wild ginseng cambium-
derived homogeneous cell line extract or culture medium on
MMP-1 expression caused by UV radiation

| Sample | Stage | Concentration (ppm or %) | % of control |
|---|---|---|---|
| | Growth | 100 | 140 |
| | | 10 | 160 |
| Dry (ppm) | Elicitation 1 | 50 | 120 |
| | | 10 | 140 |
| | Elicitation2 | 50 | 135 |
| | | 10 | 180 |
| | Growth | 50 | 100 |
| | | 10 | 165 |
| Media (%) | Elicitation 1 | 1/10 | 60 |
| | | 1/20 | 130 |
| | Elicitation2 | 1/10 | 60 |
| | | 1/20 | 200 |
| | Growth | 1/10 | 230 |
| | | 1/20 | 250 |

Figure 4:
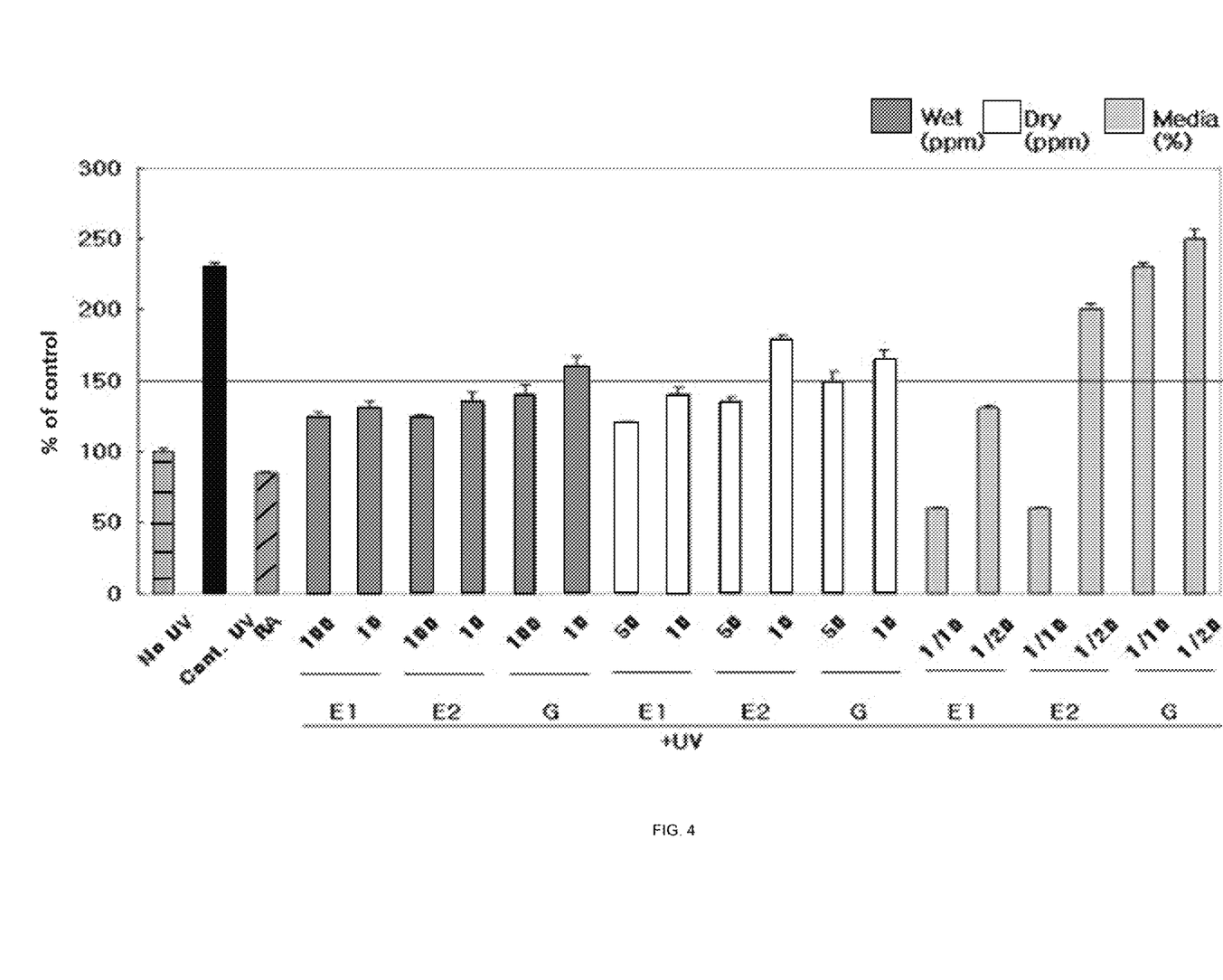

As a result, as shown in Table 13 and FIG. 4, the cell line extract and culture medium according to the present invention effectively inhibited the expression of MMP-1 compared to the negative control (Control UV), suggesting that they had the effects of preventing and reducing wrinkles. Particularly, when the NHF(p6) cells were treated with 0.1% of each of the cell line culture media of Elicitation 1, treated with raw sugar and methyl jasmonate, and of Elicitation 2, treated only with methyl jasmonate, these cell line culture media showed a very excellent effect compared to retinoic acid known to have the strong effect on wrinkle reduction.

Example 6

Measurement of Inhibitory Effect on Reactive Oxygen Species Caused by UV Radiation—Examination of Antioxidant Effect In order to examine whether reactive oxygen species that increased by UV radiation is inhibited by the extract or culture medium of the wild ginseng cambium-derived homogeneous cell line, human keratinocyte HaCaT cells (German Cancer Research Institute, Heidelberg, Germany) were dispensed in a 96-well black plate at a density of 30,000 cells/well and treated with varying concentrations of each of the samples for 3 hours. After 3 hours, the plate was washed once with HBSS, each well was treated with 50 μM DCF and incubated at 37° C. for 20 minutes. After the plate had been washed twice with HBSS, the initial absorbance of the cells was measured using a luminator. The cells were radiated with 30 mJ of UVB, cultured at 37° C. for 2 hours, and then measured for absorbance. In Table 14 below, "Control" indicates a group treated with neither the sample nor UVB, and "UVB" indicates a group treated only with UVB without adding the sample.

TABLE 14

Inhibitory effects of extract or culture
medium of wild ginseng cambium-derived homogeneous
cell line on reactive oxygen species caused by UV radiation

| Sample | Stage | Concentration (ppm or %) | % of control |
|---|---|---|---|
| Control | | | 100 |
| UVB | | | 140 |
| Wet (ppm) | Elicitation 1 | 100 | 80 |
| | | 10 | 170 |
| | Elicitation2 | 100 | 140 |
| | | 10 | 135 |

TABLE 14-continued

Inhibitory effects of extract or culture
medium of wild ginseng cambium-derived homogeneous
cell line on reactive oxygen species caused by UV radiation

| Sample | Stage | Concentration (ppm or %) | % of control |
|---|---|---|---|
| | Growth | 100 | 150 |
| | | 10 | 170 |
| Dry (ppm) | Elicitation 1 | 50 | 50 |
| | | 10 | 135 |
| | Elicitation2 | 50 | 140 |
| | | 10 | 135 |
| | Growth | 50 | 105 |
| | | 10 | 145 |
| Media (%) | Elicitation 1 | 10 | 100 |
| | | 1 | 130 |
| | Elicitation2 | 10 | 130 |
| | | 1 | 105 |
| | Growth | 10 | 110 |
| | | 1 | 120 |

Figure 5:
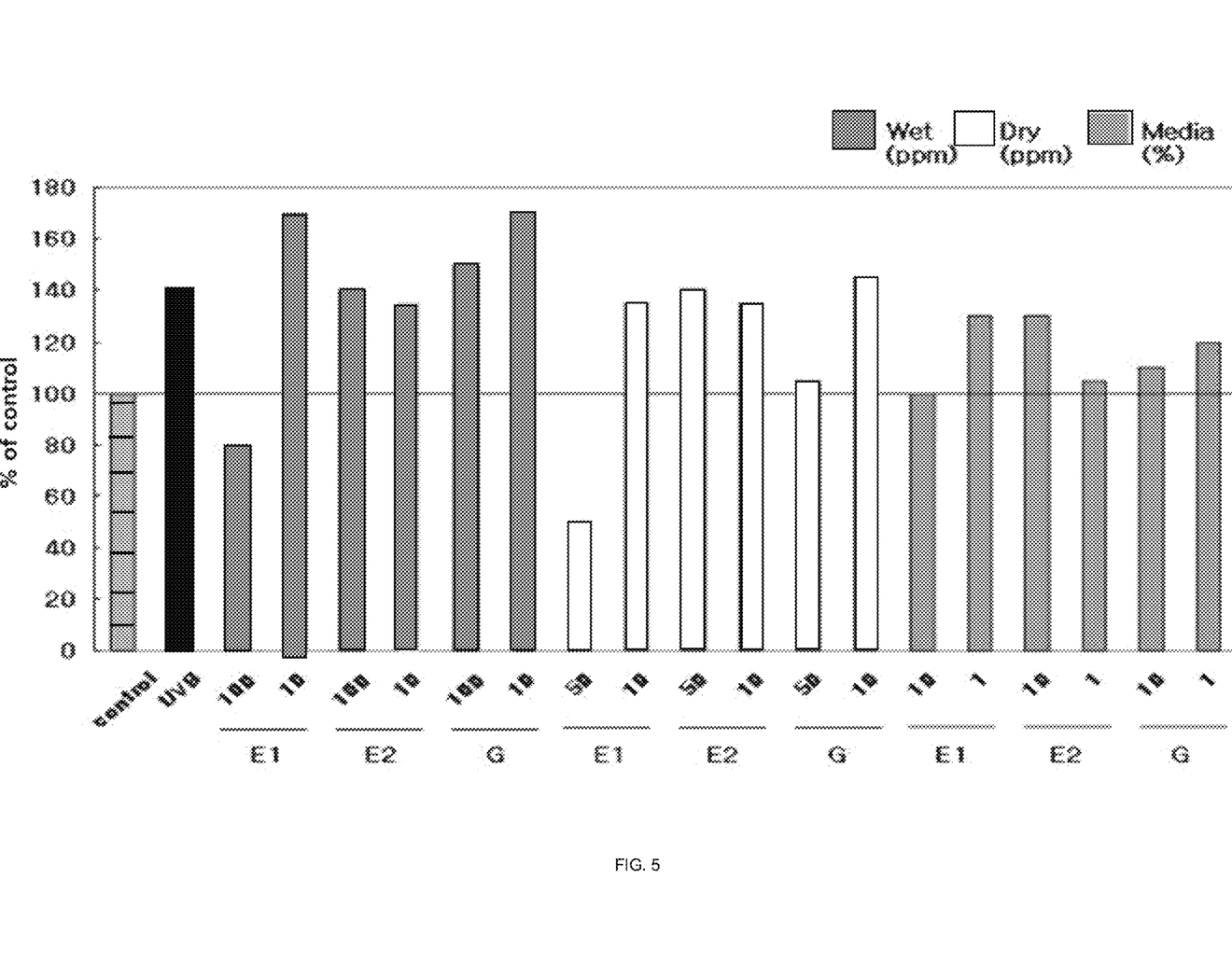

As a result, as shown in Table 14 and FIG. 5, in the cases where the inventive cell line from which the culture medium has been removed (Wet) was used and where the inventive freeze-dried cell line was used (Dry), the cell line extract of Elicitation 1 showed an excellent antioxidant effect. The cell line extract of Elicitation 2 and the cell line extract of Growth stage showed similar antioxidant effects. Also, the group treated with 50 ppm of the freeze-dried cell line extract of Elicitation 1 showed the most excellent antioxidant effect.

Example 7

Analysis of Ginsenoside Components

It is known that the ginsenoside components of wild ginseng extracts are effective in skin aging prevention and antioxidation. Thus, in order to examine whether the skin aging effects and antioxidant effects of the cell line extract and culture medium according to the present invention are attributable to the effects of such ginsenoside components, the content of ginsenosides was measured. Specifically, the wild ginseng cambium-derived homogeneous cell line prepared in Example 2 and wild ginseng were freeze-dried, and 20 mg of the freeze-dried cell line was extracted in 600 μl of methanol for 1 hour. The extract was centrifuged and the supernatant was isolated. The content of ginsenosides in the isolated extract was measured using HPLC, and the measured content was shown in comparison with standard Re, Rb1, Rb2 and Rd. Also, the culture medium of Elicitation 1 was filtrated using a 0.2-μm syringe filter, and the content of ginsenosides therein was measured using HPLC. The measured content was shown in comparison with standard Re, Rb1, Rb2 and Rd.

TABLE 15

Comparison of ginsenoside content between
wild ginseng cambium-derived homogeneous cell line and
culture medium and wild ginseng

| | Wild ginseng cambium-derived cell line | | | Culture medium of wild ginseng cambium-derived cell line | Wild giseng |
|---|---|---|---|---|---|
| | Growth | Elicitation 1 | Elicitation 2 | | |
| Ginsenoside (Rb1, Rb2, Rd, Re) | 0% | 0.003% | 0.018% | 0% | 3% |

As a result, as can be seen in Table 15, the cell line of Elicitation 2 showed the highest ginsenoside content, but ginsenoside content of the wild ginseng extract, a control group, was 167-fold higher than the ginsenoside content of the wild ginseng cambium-derived homogeneous cell line. Also, no ginsenoside was detected in the wild ginseng cambium-derived cell line of growth stage or in the cell line culture medium. This suggests that the skin anti-aging and antioxidant effects of the cell line extract and culture medium according to the present invention are not attributable to ginsenosides and that the cell line isolated according to the method of the present invention contains active ingredients that differ from those of conventional wild ginseng cells.

Example 8

Examination of Inhibitory Effects on Collagenase (MMP-1) Production Induced by UV Radiation (2)

In order to compare the anti-aging activity of the inventive wild ginseng cambium-derived cell line with the anti-aging activity of cultivated wild ginseng, the following experiment was carried out by the Kyung Hee University Skin Biotechnology Center according to the standard operating guideline of the center.

First, fibroblasts (MCTT, Korea) were seeded in a 24-well plate at a density of $2 \times 10^4$ cells/well and cultured for 12 hours to adhere to the culture plate. Then, the cells were starved in FBS-free medium for 12 hours. The cells were washed with DPBS buffer and irradiated with 100 mJ/cm$^2$ of UV at 365 nm. Then, the cells were treated with each of 1, 10 and 50 ppm of a DMSO extract (Elicitation 1) of the freeze-dried cell line of Example 2 (treated with 3-5 wt % (g/L) of raw sugar and 100 μM of methyl jasmonate) or with each of 0.05, 0.1 and 1 vol % of the culture medium of Example 2, in FBS-free medium for 24 hours. Also, positive control cells were treated with 1 μM of RA (retinoic acid), and additional control cells were treated with each of 1, 10 and 50 ppm of a DMSO extract of the freeze-dried wild ginseng root of Example 2. Then, each of the culture media was collected and centrifuged, and the amount of MMP-1 in the supernatant was determined by an ELISA assay (Amersham). The viability of the cells was measured using WST-1 solution and corrected.

Figure 6:
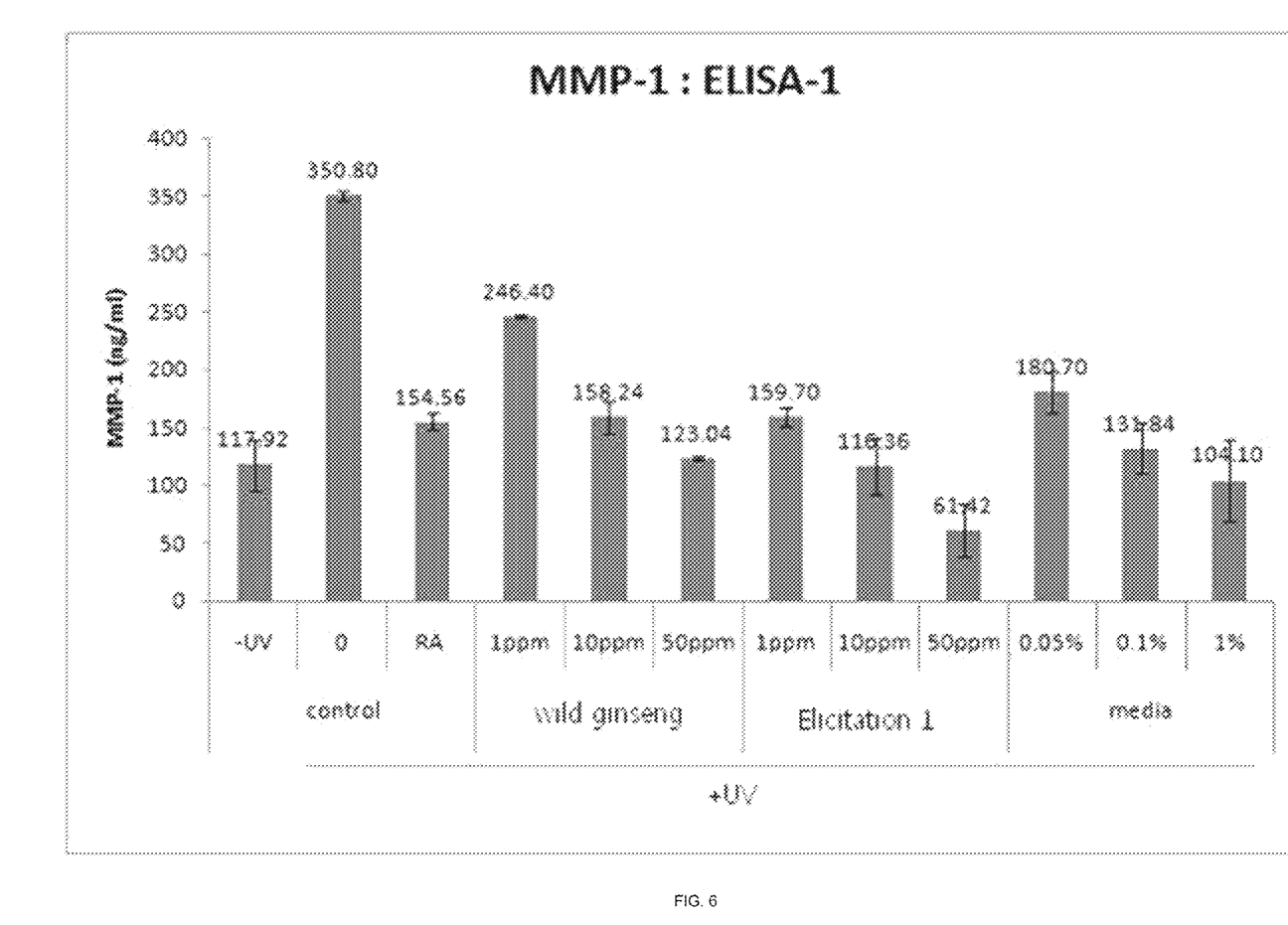
FIG. 6 is a graphic diagram showing the effect of an extract of a wild ginseng cambium-derived homogenous cell line or a culture medium of the cell line on the inhibition of MMP-1 production when inducing MMP-1 by UV radiation.

As a result, as shown in FIG. 6, the cell line extract according to the present invention showed MMP-1 inhibitory activities of about 55% (1 ppm), about 67% (10 ppm) and about 83%, and the cell line culture medium showed MMP-1 inhibitory activities of about 49% (0.05 vol %), about 63% (0.1 vol %) and 70% (1 vol %). Also, when the cells were treated with 10 ppm or 50 ppm of the cell line extract or with 0.1 vol % or 1 vol % of the culture medium, it was found that the cell line extract and the culture medium showed excellent anti-aging effects compared to the positive control RA known to have an excellent anti-aging effect.

Particularly, the cell line extract and culture medium according to the present invention showed significantly excellent effects on the inhibition of MMP-1 expression compared to the control (the freeze-dried DMSO extract of the outdoor-cultivated wild ginseng root). Specifically, the MMP-1 inhibitory activity of the cell line extract was improved by 27-51% relative to that of the cultivated wild ginseng, and the MMP-1 inhibitory activity of the cell line extract was improved by 16-27%.

Accordingly, it was found that the cell line extract and culture medium according to the present invention showed very excellent anti-aging effects compared to RA known to have excellent anti-aging effects and wild ginseng extract, suggesting that the cell line extract and culture medium according to the present invention are particularly useful as anti-aging compositions.

Example 9

Examination of Effects on Removal of Reactive Oxygen Species Induced by UV Radiation (2)

In order to compare the anti-aging activity of the inventive wild ginseng cambium-derived cell line with the anti-aging activity of outdoor-cultivated wild ginseng, the following experiment was carried out by the Kyung Hee University Skin Biotechnology Center according to the standard operating guideline of the center.

First, human keratinocyte HaCaT cells (German Cancer Research Institute, Heidelberg, Germany) were cultured in 10% FBS-containing DMEM medium. The cells were seeded in 96-well plates at a density of $3 \times 10^4$ cells/well for 12 hours to adhere to the culture plate. Then, the cells were treated with each of 1, 10 and 50 ppm of a DMSO extract (Elicitation 1) of the freeze-dried cell line of Example 2 (treated with 3-5 wt % (g/L) of raw sugar and 100 μM of methyl jasmonate) or with each of 1, 5 and 10 vol % of the culture media of Example 2 in FBS-free DMEM medium for 3 hours. Also, positive control cells were treated with 10 mM NAC(N-acetyl-cysteine), and additional control cells were treated with each of 1, 10 and 50 ppm of a DMSO extract of the freeze-dried wild ginseng root of Example 2.

Then, the cells were washed with HBSS buffer and incubated with 50 μM F-DA (HBSS) at 37° C. for 20 minutes. Then, the cells were washed twice with HBSS buffer, 30 μl HBSS was added thereto, and the cells were radiated with 200 mJ/cm$^2$ of UV at 365 nm. Then, the cells were cultured at 37° C. for 2 hours and measured for fluorescence (excitation, 485 nm; emission, 535 nm; Infinite M-200, Tecan), and the cell viability was measured using WST-1 solution and corrected. The effect of each sample on the removal of reactive oxygen species was compared with the UV-non-radiated group whose fluorescence was taken as 100.

Figure 7:
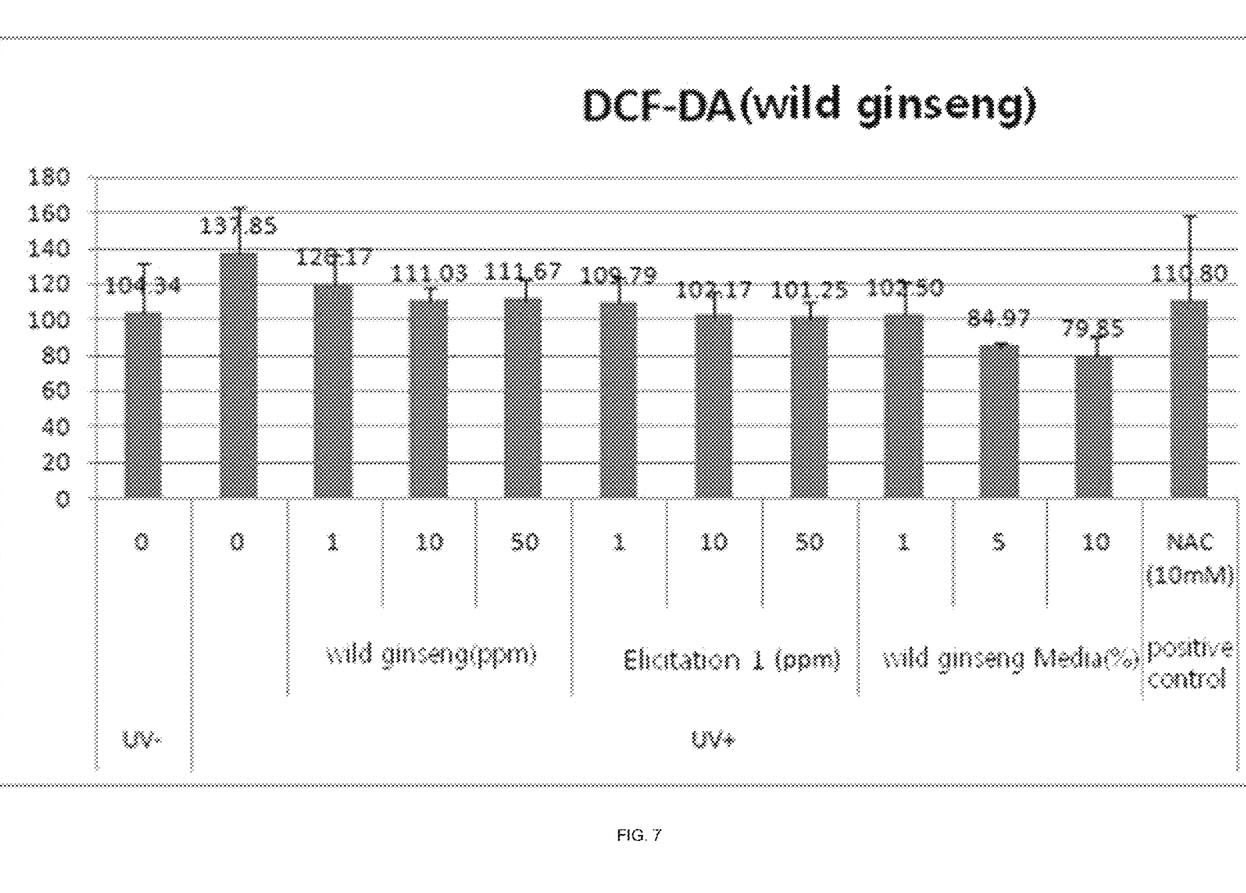
FIG. 7 is a graphic diagram showing the effect of a wild ginseng cambium-derived homogenous cell line extract or culture medium of the present invention on the removal of reactive oxygen species caused by UV radiation.

As shown in FIG. 7, when the effects of the samples on the removal of reactive oxygen species were compared with the negative control (UV-radiated group), the wild ginseng extract as the control showed an inhibitory activity of 17-26%, whereas the cell line extract and culture medium according to the present invention showed further increased inhibitory activities of 28-36% and 35-58%, respectively. Thus, it could be found that the cell line extract and culture medium according to the present invention had much more potent antioxidant effects than the cultivated wild ginseng extract.

Example 10

Preparation of Pharmaceutical Formulations

Formulation 1: Preparation of Tablet 100 mg of the cell line extract prepared in Example 2 was mixed with 100 mg of maize starch, 100 mg of lactose and 2 mg of magnesium stearate, and the mixture was compressed into a tablet according to a conventional tableting method.

Formulation 2: Preparation of Capsule Formulation 500 mg of the cell line extract prepared in Example 2 was filled in a soft gelatin capsule to prepare a capsule formulation.

Formulation 3: Preparation of Syrup Formulation 1 g of the cell line prepared in Example 1 was mixed with 10 g of isomerized sugar, 5 g of mannitol and a suitable amount of purified water, and the mixture was prepared into 100 ml of a syrup formulation according to a conventional method.

Formulation 4: Preparation of injection solution 200 mg of the cell line extract prepared in Example 2 was heated and dissolved in 200 mg of physiological saline containing polyoxyethylene hydrogenated castor oil, thus preparing an injection solution containing the extract at a concentration of 0.1%.

Example 11

Preparation of Cosmetic Formulations

Formulation 1: Preparation of Skin Lotion

| Components | wt % |
| --- | --- |
| Wild ginseng cell line extract or culture medium thereof | 0.1 |
| Glycerin | 3 |
| Butylene glycol | 2 |
| Propylene glycol | 2 |
| Carboxyvinyl polymer | 0.1 |
| PEG 12 Nonylphenyl ether | 0.2 |
| Polysorbate 80 | 0.4 |
| Ethanol | 10 |
| Triethanolamine | 0.1 |
| Antiseptics, pigment, Fragrance | q.s. |
| Purified water | to 100 |

Formulation 2: Preparation of Milk Lotion

| Components | wt % |
| --- | --- |
| Wild ginseng cell line extract and culture medium thereof | 0.5 |
| Squalene | 5 |
| Beeswax | 4 |
| Polysorbate 60 | 1.5 |
| Sorbitan sesquioleate | 1.5 |
| Liquid paraffin | 0.5 |
| Caprylic/Capric triglyceride | 5 |
| Glycerin | 3 |
| Butylene glycol | 3 |
| Propylene glycol | 3 |
| Carboxyvinyl polymer | 0.1 |
| Triethanolamine | 0.2 |
| Antiseptics, pigment, Fragrance | q.s. |
| Purified water | to 100 |

Formulation 3: Preparation of Nourishing Cream

| Components | wt % |
| --- | --- |
| Wild ginseng cell line extract or culture medium thereof | 2 |
| Beeswax | 10 |
| Polysorbate 60 | 1.5 |
| PEG 60 hydrogenated Caster oil | 2 |
| Sorbitan sesquioleate | 0.5 |
| Liquid paraffin | 10 |
| Squalene | 5 |
| Caprylic/Capric triglyceride | 5 |
| Glycerin | 5 |
| Butylene glycol | 3 |
| Propylene glycol | 3 |
| Triethanolamine | 0.2 |
| Antiseptics, pigment, Fragrance | q.s. |
| Purified water | to 100 |

Formulation 4: Preparation Of Massage Cream

| Components | wt % |
| --- | --- |
| Wild ginseng cell line extract or culture medium thereof | 5 |
| Beeswax | 10 |
| Polysorbate 60 | 1.5 |
| PEG 60 hydrogenated Caster oil | 2 |
| Sorbitan sesquioleate | 0.8 |
| Liguid paraffin | 40 |
| Squalene | 5 |
| Caprylic/Capric triglyceride | 4 |
| Glycerin | 5 |
| Butylene glycol | 3 |
| Propylene glycol | 3 |
| Triethanolamine | 0.2 |
| Antiseptics, pigment, Fragrance | q.s. |
| Purified water | to 100 |

Formulation 5: Preparation of Pack

| Components | wt % |
| --- | --- |
| Wild ginseng cell line extract or culture medium thereof | 5 |
| Polyvinyl alcohol | 13 |
| Carboxymethylcellulose sodium | 0.2 |
| Glycerin | 5 |
| Allantoin | 0.1 |
| Ethanol | 6 |
| PEG 12 Nonylphenyl ether | 0.3 |
| Polysorbate 60 | 0.3 |
| Antiseptics, pigment, Fragrance | q.s. |
| Purified water | to 100 |

Example 12

Preparation of Functional Food: Preparation of Functional Beverage

Preparation 1

200 mg of the cell line prepared in Example 1 was dissolved in 96 ml of water, and then 500 mg of vitamin C as a supplement, 1 g of each of citric acid and oligosaccharide as flavor enhancers and 0.05 g of sodium benzoate as a preservative were added thereto. Then, purified water was added thereto, thus preparing 100 ml of a functional beverage.

Preparation 2

200 mg of the cell line extract prepared in Example 2 was dissolved in 96 ml of water, and then 500 mg of vitamin C as a supplement, 1 g of each of citric acid and oligosaccharide as flavor enhancers and 0.05 g of sodium benzoate as a preservative were added thereto. Then, purified water was added thereto, thus preparing 100 ml of a functional beverage.

INDUSTRIAL APPLICABILITY

As described above, the composition according to the present invention has minimized side effects compared to existing anti-aging agents and antioxidants, and thus is safe for the skin. Also, the composition of the present invention shows an antioxidant effect of inhibiting reactive oxygen species caused by exposure to UV radiation that is the major cause of skin aging, and it can effectively reduce or inhibit aging-related factors. Thus, the composition of the present invention is useful for the prevention and inhibition of aging.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

The invention claimed is:

1. A method of inhibiting aging or oxidation of the skin of a subject, comprising:
    administering, to the skin of the subject, a composition comprising one or more of an extract, a culture or a lysate of a homogeneous preparation of innately undifferentiated cells of a cell line derived from a cambium of *Panax ginseng*, thereby inhibiting the aging or oxidation of the skin of the subject.

2. The method according to claim 1, wherein the cell line is additionally characterized in that:
    (a) the cells are present as single cells during suspension culture;
    (b) the cells have low sensitivity to shear stress in a bioreactor compared to cell lines derived from tissues other than the cambium of *Panax ginseng*; and
    (c) the cells have a higher growth rate than those of cell lines derived from tissues other than the cambium of *Panax ginseng* and are cultured stably.

3. The method according to claim 1, wherein the cell line is obtained using an isolation method comprising the following steps of:
    (a) obtaining a storage root tissue containing the cambium of *Panax ginseng*;
    (b) applying osmotic stress to the obtained cambium-containing storage root tissue, and then culturing the cambium-containing storage root tissue in a IAA (Indole-3-acetic acid)- or IBA (Indole-3-butyric acid)-containing medium, thereby inducing a cambium-derived cell line; and
    (c) collecting the induced cambium-derived cell line.

4. The method according to claim 3, wherein the culture is obtained by additionally culturing the cell line in a medium which contains 3-5 wt. % of raw sugar or sugar; or at least one substance selected from the group consisting of methyl jasmonate, fungal extract, bacterial extract, yeast extract, chitosan, glucomannan, glucan, phenylalanine, benzoic acid, salicylic acid, arachidonic acid, STS (staurosporine), mevalonalonate N-benzolyglycine, ABA (aminobenzoic acid), SNP (sodium nitroprusside), IPP (isopentenyl pyrophosphate), BHT (butylated hydroxytoluene), CCC (chlorocholine chloride), ethephon, hippuric acid, ammonium ceric nitrate, $AgNO_3$, vanadyl sulfate, p-aminobenzoic acid, brassinosteroids, sodium alginate, and sodium acetate.

5. The method according to claim 1, wherein the *Panax ginseng* is wild ginseng or ginseng.

6. The method according to claim 1, wherein the extract is obtained using a solvent selected from the group consisting of distilled water, alcohol, acetone, DMSO (dimethyl sulfoxide), and mixtures thereof.

7. The method according to claim 1, wherein the extract is obtained by fractionating the cells sequentially with distilled water, methanol and acetone.

8. The method according to claim 1, wherein the cell line is obtained using an isolation method comprising the following steps of:
    (a) obtaining a storage root tissue containing the cambium of *Panax ginseng*;
    (b) applying osmotic stress to the obtained cambium-containing storage root tissue, and then culturing the cambium-containing storage root tissue in a IAA (Indole-3-acetic acid)-containing medium, thereby inducing a cambium-derived cell line; and
    (c) collecting the induced cambium-derived cell line.

9. The method according to claim 8, wherein the culture is obtained by additionally culturing the cell line in a medium which contains 3-5 wt. % of raw sugar or sugar; or methyl jasmonate.

* * * * *